United States Patent [19]

Prillieux et al.

[11] Patent Number: 4,618,458
[45] Date of Patent: Oct. 21, 1986

[54] SULPHONIC ACIDS AND SULPHONATES

[75] Inventors: Marcel Prillieux, Mont-Saint-Aignan; Robert M. Laurent, Bois Guillaume; Robert Tirtiaux, Mont-Saint-Aignan, all of France

[73] Assignee: Exxon Research & Engineering Co., Florham Park, N.J.

[21] Appl. No.: 203,169

[22] Filed: Nov. 3, 1980

Related U.S. Application Data

[63] Continuation of Ser. No. 973,032, Dec. 26, 1978, abandoned.

[30] Foreign Application Priority Data

Dec. 23, 1977 [GB] United Kingdom ............... 53638/77

[51] Int. Cl.$^4$ ........................................... C07C 143/24
[52] U.S. Cl. ................................................ 260/505 P
[58] Field of Search .................................... 260/505 P

[56] References Cited

U.S. PATENT DOCUMENTS 4,153,627  5/1979  Delbende et al. ............... 260/505 P Primary Examiner—Alan Siegel
Attorney, Agent, or Firm—F. T. Johmann; P. C. Bawden; J. J. Mahon

[57] ABSTRACT

Purification of sulphuric acid rich sulphonic acids particularly those prepared by oleum sulphonation, by water washing, treatment with an olefine and final heat treatment.

6 Claims, No Drawings

SULPHONIC ACIDS AND SULPHONATES

This is a continuation of application Ser. No. 973,032, filed 12/26/78, now abandoned.

German Patent Application No. 2707414, corresponding to U.S. Pat. No. 4,153,627, describes alkaryl sulphonic acids containing at least 1% by weight of an olefine whose presence improves the thermal and colour stability of the acids and reduces their sludge and sulphuric acid content. In some instances the addition of the olefine has also been found to obviate the need for the complex purification techniques that have hitherto been used.

Whilst these techniques have proved satisfactory, particularly in the preferred process of German Application No. 2707414 where sulphonation is achieved with a mixture of sulphur dioxide and sulphur trioxide, we have found that when the alkaryl sulphonic acid is particularly rich in sulphuric acid, as can occur with acids produced by oleum sulphonation, the residual sulphuric acid content after olefine treatment can be unacceptably high. We have found that this may be overcome if the sulphonic acid is washed prior to addition of the olefine and is heat treated following the addition of the olefine.

The present invention therefore provided a process for the purification of alkaryl sulphonic acids comprising treating a crude sulphonic acid with from 1% to 30% by weight, based on the weight of the alkylate from which the sulphonic acid is obtained, of water, adding at least 1% by weight, based on the weight of the alkylate, of an olefin and subsequently heating the sulphonic acid containing the olefine to a temperature in the range of 100° C. to 150° C. for at least 15 minutes in which the aqueous component is removed prior to the heating.

The techniques of the present invention may be applied to alkaryl sulphonic acids obtained by any sulphonation process. They are however primarily directed at the purification of sulphonic acids which contain more than 2 wt.%, particularly those containing more than 3 wt.% of sulphuric acid. The techniques of the present invention are especially useful in the purification of sulphonic acids prepared by oleum sulphonation.

The techniques of our invention are generally applicable to alkylaryl sulphonic acids including acids derived from alkylated mono- or poly-nuclear aromatic compounds known as alkylates. The invention is primarily concerned with sulphonic acids derived from mono-nuclear aromatic compounds; the aromatic nucleus may contain the single alkyl group as in the alkyl benzenes or two alkyl groups such as in the alkyl toluenes or the dialkyl benzenes or three alkyl groups such as for example in the alkyl xylenes. Thus the sulphonic acid may be of the formula:

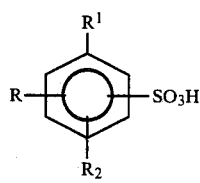

where one or both of $R^1$ and $R^2$ may be hydrogen or hydrocarbyl groups and R is an alkyl group which preferably contains 7 to 30 carbon atoms and may be straight or branched chain. Although the techniques of our invention are applicable to sulphonic acids in which R is a comparatively short chain alkyl group such as from $C_7$ to $C_{15}$ they prove especially useful with the sulphonic acids in which R is longer chain such as from $C_{20}$ to $C_{30}$ which require special purification techniques. We find the techniques of our invention to be particularly suited to the production of sulphonic acids based on alkyl aryl compounds in which the alkyl group contains from 20 to 30 carbon atoms. Throughout this specification where reference is made to a number of carbon atoms this is the average number since many of the materials are in fact mixtures of compounds containing different numbers of carbon atoms.

After sulphonation the reaction mixture is generally diluted with hexane and where a process that yields sulphonic acids rich in sulphuric acid such as oleum sulphonation is used we prefer that the diluted reaction mixture be allowed to stand for sulphuric acid to settle. Following this from 1% to 30%, preferably 5% to 15% of water by weight based on the weight of the alkylate from which the sulphonic acid is derived is added, the mixture agitated and conveniently is then allowed to stand to allow settlement of the aqueous layer which may then be removed by decantation.

For a sulphonic acid to be commercially acceptable it should contain no more than 0.5 wt.% sulphuric acid and we have found that generally this may be achieved by treatment with an olefine providing the acid contains no more than 3 wt.%, preferably 2 wt.% of sulphuric acid prior to treatment. We therefore prefer that the water treatment reduce the sulphuric acid content of the sulphonic acid to no more than 3% by weight.

At least 1% by weight of the alkylate from which the sulphonic acid is derived of an olefine is then added to the sulphonic acid. For economic reasons we prefer to use as little olefin as possible, preferably less than 10%; at least 1% by weight should be used, and we prefer to use from 2% to 10% by weight, more preferably from 3% to 6% by weight.

Any suitable olefin may be used in the technique of our invention, but we prefer to use a liquid olefin and the choice is generally a question of economics. The particular olefin that should be used will depend upon the nature of the sulphonic acid and the preferred olefine may be found by experimentation to determine which olefine combines effective reduction of sulphuric acid with improved colour stability in the particular sulphonic acid. We have found, for example, that an olefine of molecular weight from 294 to 336 is most suitable for use with a $C_{24}$ alkyl benzene sulphonic acid. We prefer to use a monoolefine since diolefines are more expensive and although they impart some improvement to the sulphonic acid and sulphonates, we find them less effective than monoolefines.

We have found that propylene oligomers especially trimers, tetramers and octamers are particularly suitable, more so since they tend to be readily available. Since for many applications sulphonic acids are used as solutions in oil it is preferred that the olefin be oil soluble and thus olefins containing from 9 to 30 carbon atoms are especially suitable; those containing from 12 to 24 carbon atoms being most preferred. The quantity of olefin that is used depends upon the degree of stability required, the nature of the sulphonic acid and the sulphuric acid content. As mentioned, sulphonic acids are often supplied as concentrates in an oil and in certain instances the olefin may replace part or all of the oil and in this instance more than 10% will be present.

No special blending techniques are required and the olefin is incorporated after the water washing in any appropriate manner. We find that within normal operating limits the temperature at which the olefine is mixed with the sulphonic acid is not critical.

After addition of the olefine, the sulphonic acid containing the olefine is heat treated to ensure the necessary removal of the sulphuric acid. The heat treatment that should be used consists of heating to a temperature in the range 100° C. to 150° C. for at least 15 minutes. We generally find that is it not necessary to heat for more than one hour and we have found that heating to between 120° C. and 140° C. for about 30 minutes is particularly effective.

We have found in certain instances that using our techniques the reduction in sludge and sulphuric acid, even in the sulphonation of alkyl aromatics with longer alkyl chains, is sufficient that it is not necessary to wash with aqueous hydrochloric acid solution to remove sulphuric acid as has previously been necessary. This leads to a considerable simplification of the process for manufacturing sulphonic acids.

Sulphonic acids are generally neutralised to give sulphonates that are used as detergents where they are usually used as their salts with alkali metals, generally sodium, or with quaternary nitrogenous cations. Sulphonates with the longer alkyl chain lengths may be used as emulsifiers in the formation of oil in water emulsions as for example in lubricating oils for metal working; here again the sulphonates are usually the sodium or ammonium salts including ethoxylated ammonium salts. Sulphonic acids are also used in the production of highly basic sulphonates of the type that are used as detergent additives in lubricating oils. In this instance the sulphonates are normally highly basic calcium, magnesium or barium salts. The sulphonic acids are generally supplied as solutions in oils, which may be concentrates and the nature of the oil is not important although we prefer to use the well-known paraffinic mineral oils. The concentrates preferably contain from 50% to 95% by weight, usually 65% to 90% by weight of the sulphonic acid.

The present invention is illustrated but in no way limited by the following Examples.

EXAMPLE 1

A $C_{24}$ alkyl benzene of molecular weight from 405 to 435 that had been obtained by alkylating benzene with a $C_{24}$ average propylene oligomer using a Friedel Crafts catalyst was sulphonated with oleum at 50° C. for 30 minutes. The sulphonated product was diluted with hexane, agitated and then left to settle to allow separation of impurities and sulphuric acid. The residual sulphuric acid content after settling was 12 wt.% based on the weight of sulphonic acid.

In two of a series of four comparative experiments the sulphonic acid was washed with water (12.5 wt.% based on the weight of the $C_{24}$ alkyl benzene) at 25° C. and allowed to settle for 2 hours. In one experiment 6 wt.%, based on the weight of the alkylate of benzene of the $C_{24}$ average proplyene oligomer used in the alkylation, was added after washing and before heat treatment. In the other two experiments the comparison was repeated without the washing and heat treatment steps.

In a fifth test 10 wt.% of the olefine was added after washing and the olefine containing acid heat treated.

The results were as follows:

| Amount olefine added | Washing and Heat Treatment | Residual $H_2SO_4$ wt. % on Sulphonic Acids |
|---|---|---|
| 0 | NO | 12.0 |
| 6 Wt. % | NO | 11.7 |
| 0 | YES | 1.5 |
| 6 Wt. % | YES | 0.05 |
| 10 Wt. % | YES | 0.05 |

EXAMPLE 2

100 parts by weight of various alkylates were sulphonated with oleum under the same conditions as used in Example 1. The sulphonated material was diluted with hexane (100 parts by weight) and allowed to settle for from 2 to 3 hours. 12.5 parts by weight of water were then added and the mixture agitated and then allowed to settle. Finally the olefin used in Example 1 was added and the mixture heat treated at 130° C. for 15 minutes.

The quantities of sulphonic acid and sulphuric acid present after first settling, after water washing and after olefin addition and heat treatment were measured and found to be as follows:

| Alkylate | $C_{24}$ Branched Chain Monoalkylate | Di $C_{13}$ Straight Chain Alkylate | Straight Chain Monoalkylate MW = 450 |
|---|---|---|---|
| Sulphonation Conditions | 100 parts by weight oleum | 160 parts by weight oleum | 100 parts by weight oleum |
| Olefin addition | 6 wt. % on alkylate | 8 wt. % on alkylate | 8 wt. % on alkylate |
| Composition after settling | 78.2 wt. % 12.7 wt. % 9.1 wt. % | 81.0 wt. % 11.2 wt. % 7.8 wt. % | 82.1 wt. % sulphonic acid 10.2 wt. % sulphuric acid 7.7 wt. % unsulphonated |
| After water treatment | 92.2 wt. % 1.4 wt. % 8.4 wt. % | 91.1 wt. % 2.0 wt. % 6.9 wt. % | 88.4% sulphonic acid 2.1% sulphuric acid 9.5% unsulphonated |
| After olefin addition and Heat treatment | 88.8 wt. % 0.05 wt. % 11.15 wt. % | 86.2 wt. % 0.1 wt. % 13.7 wt. % | 83.7 wt. % sulphonic acid 0.1 wt. % sulphuric acid 16.2 wt. % unsulphonated |

We claim:

1. In an oleum sulfonation process wherein an alkaryl alkylate, having alkyl groups of 20 to 30 carbon atoms and an aryl group selected from the group consisting of benzene, toluene and xylene, is treated with oleum to form a sulfonated product, settling said sulfonated product to separate impurities and sulfuric acid to thereby give a crude alkaryl sulfonic acid containing more than 3 wt. % sulfuric acid, the improvement which comprises washing said crude alkaryl sulphonic acid, to reduce the sulfuric acid content to no more than 3 wt. % sulfuric acid, with from 1% to 30% by weight, based on the weight of the alkylate from which the sulphonic acid is derived, of water, allowing the resulting mixture to separate and removing the aqueous layer; adding 2 to 10% by weight based on the weight of the alkylate from which the sulphonic acid is derived of a liquid oil soluble monoolefin of 9 to 30 carbon atoms and subsequently heating the sulphonic acid containing the olefin to a temperature in the range of about 100° C. to about 150° C. for at least 15 minutes to about one hour, and recovering a purified sulfonic acid containing less than 0.5 wt. % sulfuric acid.

2. A process according to claim 1, in which hexane is added to said sulfonated product before said settling, and said water washing reduces the sulfuric acid content to less than 2 wt. %.

3. A process according to claim 2, in which the olefin has a molecular weight of from 294 to 336.

4. A process according to claim 3, in which heat treatment is carried out at a temperature between 120° C. and 140° C. for about 30 minutes.

5. A process according to claim 3, wherein said olefine is propylene oligomer.

6. In a process wherein $C_{24}$ alkyl benzene sulfonate is prepared by oleum sulfonation of $C_{24}$ alkyl benzene alkylate followed by mixing the oleum treated $C_{24}$ alkyl benzene with hexane and allowing the mixture to settle to separate out impurities and sulfuric acid to thereby obtain a crude sulfonate containing more than 3 wt. % sulfuric acid, washing said crude sulfonate, to reduce the sulfuric acid content to no more than 3 wt. % sulfuric acid, with 1 to 30 wt. % water, based on weight of said alkylate, allowing the mixture to separate and then removing the aqueous layer, adding 2 to 10 wt. % $C_{24}$ propylene oligomer oil soluble monoolefin, based on weight of said alkylate, and heating to 100° to 150° C. for at least 15 minutes to about one hour, and recovering a purified $C_{24}$ alkyl benzene sulfonate containing less than 0.5 wt. % sulfuric acid.

* * * * *